United States Patent [19]
Elling et al.

[11] Patent Number: 5,750,389
[45] Date of Patent: May 12, 1998

[54] PURIFIED SACCHAROSE-SYNTHASE, PROCESS FOR ITS PRODUCTION AND ITS USE

[75] Inventors: Lothar Elling, Aachen; Maria-Regina Kula, Niederzier, both of Germany

[73] Assignee: Forschungszentrum Julich GmbH, Julich, Germany

[21] Appl. No.: 367,178

[22] PCT Filed: Jun. 26, 1993

[86] PCT No.: PCT/DE93/00562

§ 371 Date: Jan. 6, 1995

§ 102(e) Date: Jan. 6, 1995

[87] PCT Pub. No.: WO94/01540

PCT Pub. Date: Jan. 20, 1994

[30] Foreign Application Priority Data

Jul. 1, 1992 [DE] Germany .............................. 42 21 595.1
Feb. 16, 1993 [DE] Germany .............................. 43 04 558.8

[51] Int. Cl.⁶ .................................................. C12N 9/10
[52] U.S. Cl. ............................ 435/193; 435/89; 435/90; 435/91.1; 435/183; 435/195
[58] Field of Search ................................. 435/193, 195, 435/183, 89, 90, 91.1

[56] References Cited

PUBLICATIONS

Journal of the Chinese Biochemical Society, vol. 17, No. 1, 1988, pp. 42–51, Rong–Huay Juang et al "Purification of Rice Grain Sucrose Synthetase by Preparative Electrophoresis".

Applied Biochemistry and Biotechnology, vol. 23, No. 2, Feb. 1990, pp. 155–170, Sharon L. Haynie et al, "Enzyme Catalyzed Organic Synthesis of Sucrose and Trehalose With in Situ Regeneration of UDP–Glucose".

Plant Physiology, vol. 45, 1970, pp. 782–786, Deborah P. Delmer et al, "The Biosynthesis of Sucrose and Nucleoside Diphosphate Glucoses in *Phaselous aureus*".

Wong et al, J. Org. Chem., vol. 47, (1982), pp. 5416–5418.

J. Org. Chem., 1990, 55, 1834–1841, Simon et al, Convenient Synthesis of Cytidine 5'–Triphosphate, Guanosine, 5'–Triphosphate, and uridine 5'–Triphosphate and Their Use in the Preparation of UDP–Glucose, UDP–Glucoronic Acid, and GDP–Mannose.

Journal of Biological Chemistry, vol. 245, No. 1, pp. 188 to 197, Jan. 10, 1970, Grimes, W.J. et al, "Sucrose Synthetase from *Phaselous aureus* Seedlings".

Analytical Biochemistry 202, 215 to 238 (1992), Ichikawa, Yoshitaka et al, "Enzyme–Catalyzed Oligosaccharide Synthesis";.

J. Org. Chem., 1992, 57, 152 to 157, Heidlas, Jurgen E. et al, "Practical Enzyme–Based Syntheses of Uridine 5'–Diphosphogalactose and Uridine 5'–Diphospho–N–acetyl–galactosamine on a Gram Scale".

*Primary Examiner*—Leon B. Lankford, Jr.
*Attorney, Agent, or Firm*—Herbert Dubno; Jonathan Myers

[57] ABSTRACT

Nucleotide sugars, especially UDP, ADP, CDP or TDP saccharoses can be enzymatically obtained by the reaction of nucleoside diphosphates with di or trisaccharides with a saccharose synthase in which the virtual absence of nucleoside phosphatases (0.1% or less) can be ensured by special purification methods and sensitive detection. The purification of the raw extract, obtained preferably from rice grains, comprises especially the application of the ultra-filtered extract containing 50 mM KCl with a pH 8 on a sepharose Q column and a gradient elution out of the column at a pH 8 with 50 to 500 mM KCl.

7 Claims, 11 Drawing Sheets

1-UMP
2-UDP Glc
3-UDP Gal
4-UDP

PURIFIED SACCHAROSE-SYNTHASE, PROCESS FOR ITS PRODUCTION AND ITS USE

BACKGROUND OF THE INVENTION

Sucrose-synthase (Glycosyltransferase EC2.4.1.13 UDPG: D-Fructose-2-glucosyltransferase) is an enzyme which has been long known and is especially widespread in plants (e.g., wheat, rice, corn, sugar beets, etc.) see Y. Milner and others in "Nature" 206 (1965), Page 825; the function of this enzyme as a catalyst in the production of activated sugars in the metabolism of plants has been extensively studied and compendia have been produced (Avigad, G in Loewus, F.A. et al. (eds.) Encyclopedia of Plant Physiology New Series Vol. 13A, Carbohydrates I, Intracellular Carbohydrates, Springer-Verlag, Berlin 1983, pages 217–347). The enzyme catalyzes in vivo the splitting of sucrose according to the following equation:

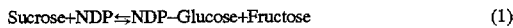

$$\text{Sucrose} + \text{NDP} \rightleftharpoons \text{NDP-Glucose} + \text{Fructose} \quad (1)$$

in which N stands for a Nucleoside, such as uridine, thymidine, cytidine, guanosine and adenosine, and NDP is nucleoside diphosphate.

Purification and characteristics of the enzyme have been described inter alia by T. Nomura et al in Arch. Biochem. Biophysics 156 (1973), pages 644–652, which gives a yield of 8.8% at 11.4 fold purification by ammonium sulfate precipitation and column chromatography on DEAE-Cellulose and Neusilin $(MgO+Al_2O_3+2SiO_2)$ and $K_m$-values for synthase reaction and splitting reaction are given.

Recently, S.L. Haynie and G.M. Whitesides have reported in Appl. Biochem. & Biotechnol. 23 (1990) about a sucrose-synthase purified by an ammonium sulfate precipitation based process and its use for the sucrose synthesis by reaction of UDP-Glucose and Fructose.

That describes the limited stability of the enzyme (page 158), especially of highly purified enzyme preparations (page 160) as well as the drawback of highly stabilized enzyme preparations of reduced purity based upon byproduct activity, especially of phosphoglucomutase and the consequent low activity requirement of the use of larger gel volume (of the gel immobilized enzyme). R.H. Juang and others describe in J. Chinese Biochem. Soc. 17 (1988) 42–51. A sucrose-synthase purification by column chromatography and electrophoresis is disclosed with 38-times purification which is carried out depending upon the protein composition.

In spite of the long known manner functioning of sucrose-synthase and the purification process, the production of activated sugars according to the above equation has not hitherto been economically utilized although the sucrose-synthase is commercially available and activated sugars as well as disaccharides and oligosaccharides are of considerable significance in sugar chemistry.

Mono-,. Oligo- and Polysaccharides have multiple functions as antigen determinants, in cell-cell recognition, in cell differentiation and as binding cites for toxins, bacteria and viruses.

A compilation of the production and use can be found in S. David and others in Advances in Carbohydrate Chem. A. Biochem. 49 (1991), 175–237. Y. Ichikawa and others present in ANal. Biochem. 202 (1992) 215–238 different reaction mechanisms. As "large scale synthesis", however, especially the reaction of sugar-1-phosphate (especially glucose-1-phosphate) with nucleoside triphosphate, especially with UTP in the presence of pyrophosphorylase, reference may be had to C.H. Wong and others (J. Org. Chem. 47 (1982) 5416–18) which describes a multistage enzymatic synthesis of nucleotide sugars.

This synthesis according to C.H. Wong is also described as the method of choice by Toone and Whiteside in Am. Chem. Soc. Sympos. Sr. 466 (1991) 1–22.

SUMMARY OF THE INVENTION

It has been surprisingly found that sucrose synthase isolate (especially of commercially available enzyme contained generally more or less high proportions of nucleotide-phosphatases and that the presence of them, even in small amounts, is so greatly detrimental to the synthesis of NDP Glucose and homologous compounds that the confirmed synthesis suitability of sucrose synthesis could not be recognized heretofore.

By appropriate purification methods and sensitive phosphatase determinations, a sucrose synthetase has been developed which is surprisingly stable and enables a clean single stage synthesis reaction according to Reaction (1).

The subject of the invention is, accordingly, a purified sucrose synthase in which its HPLC chromatogram in which in its HPLC chromatogram, nucleotide phosphatases are no longer detectable (<0.1%).

Further characteristics of the invention are given in the following description.

As sources for the sucrose-synthase, serve especially rice, corn or wheat grains which can be sprouted or which have sprouted and are mechanically disintegrated. The aqueous raw extract thereby recovered is subjected either to a PEG-precipitation (A) or a distribution in an aqueous 2-phase system (B). In (A), a fractional precipitation can be carried out in which initially (A1) relatively low molecular weight PEG (polyethylene glucose; M≧1000) and reduced PEG concentrations are utilized for the precipitation of accompanying proteins (EG with 5% PEG 4000) while the sucrose synthase remains in the supernatant; the latter is then precipitated in a second step (A2) with increased PEG concentration and from the precipitate dissolved out with 200 mM Hepes Buffer (pH 7.2). The precipitation (A2) is not necessarily required and can, as simplification of the process and yield increase, be omitted as has been indicated further below.

The molecular weight of the PEGs in the PEG-precipitation can be varied with corresponding change in the PEG percentage.

The sucrose-synthase which is again brought into solution or the supernatant or the enzyme containing phase of the extraction is advantageously after an Adsorption on Sephadex ASO and stepwise elution at pH 7.2 (set with Hepes-NaOH) with 100 mM KCl and 300 mM KCl and change of buffers as well as ultrafiltration loaded onto a sepharose-Q-column and subjected to a linear gradient elution with 50–500 mM KCl at pH 8 (200 mM Hepes-NaOH) and chromatographed on a gelfiltration column.

Especially important is the treatment step on the Sepharose Q column with gradient elution as described. In this manner, one obtains purified sucrose-synthase whose nucleotide phosphatase content <0.1%, i.e. in a phosphatase-test of the enzyme preparation nucleotide phosphatase is no longer detectable.

The sucrose synthase purified in accordance with the invention may be used especially for enzymatic synthesis of activated glucose and activated glucose derivatives by splitting of disaccharides, trisacoharides or oligosaccharides derivatives with nucleosidediphosphates. The resulting products, for example, UDP-glucose, TDP-glucose and CDP-glucose are important starting materials for the enzymatic and/or chemical preparations of activated desoxy sugars and their derivatives. A further example of the above-described use is the enzymatic splitting of 2-Desoxysaccharose with sucrose-synthase with the use of Nucleosidediphosphates, e.g. UDP or TDP. In combination with other enzymes, for example, UDP-glucose epimerase and galactosyltransferase, sucrose-synthase can be used for cyclic regeneration of e.g. UDP-glucose. Thus an enzymatic synthesis is carried out of a disaccharide derivative like, for example, N-acetyllactosamine (LacNAc) with three enzymes. In comparison with published enzymatic synthesis of LacNAc (Wong and others J. Org. Chem. 47 (1982) 5416–5418, an economic advantage is obtained because of reduction in the number of enzymes.

Sucrose-synthase of the invention purified in accordance with the invention is also usable for the synthesis of glucosides as well as their derivative. Thus UDP-glucose or activated glucose derivatives are transferred to acceptor molecules with at least one hydroxyl group. For example, for sugar molecules as acceptors include the kentoses the isomers of D-fructose, e.g. D-psicose, D-tagatose and L-sorbose, as well as their derivatives, e.g. 5, 6-didesoxy-5-keto-D-fructose and 6-Desoxy-L-sorbose. Examples of sugar molecules as acceptors as aldoses are L-arabinose, D-lyxose, D-mannose as well their derivatives, e.g. 1,6-Anhydroglucose.

Di-, Tri- and Oligosaccharides are also acceptor molecules, e.g. lactulose, isomaltulose and raffinose. Other hydroxyl group containing acceptor molecules which do not belong to the class of sugars are especially heterocyclic compounds with at least one hydroxyl group on the heterocyclic ring and/or in a side chain found thereon, e.g. 1-ethyl-3-hydroxy-pyrrollidine or A-(2-hydroxyethyl)piperidine.

BRIEF DESCRIPTION OF THE DRAWINGS

The process of the invention is described in detail in the following Examples. Reference is made to the accompanying drawings:

FIG. 5 or the invention; FIG. 6);

EXAMPLE 1

Isolation of the Saccharose-Synthase 800 g of rice grains are caused to swell overnight in Hepes-NaOH buffer pH 7.2 and are then disintegrated in a Waring Blender for 1.5 minutes. Thereafter, following homogenization with a hand mixer for a further 3 minutes, the pellet is precipitated in a centrifuge (Sorvall GS3, 20 min, 5000 rpm 4° C.). Then the protein in the supernatant is precipitated fractionally with PEG 4000 (5 and 20% PEG). The pellet after the 20% PEG precipitation is dissolved in buffer and bound to sephadex A50 in a batch adsorption. 200 ml of sephadex-A50-Gel is charged with about 4 g protein. The stepped elution is begun with 300 ml Hepes-NaOH pH 7.2 and 300 ml Hepes-NaOH pH 7.2 with 100 mM KCl. The enzyme is eluted with two volumes (100 ml) Hepes-NaOH pH 7.2 with 300 mM KCl.

After reverse buffering and ultrafiltration, this fraction was charged onto a Sepharose-Q-column (Hepes-NaOH pH 8.0 with 50 mM KCl) and eluted with a linear gradient (50 nM–500 mM KCl in Hepes-NaOH 200 mM pH 8.0) the collected enzyme fraction is finally chromatographed in a gelfiltration column (superdex 200 prep grade).

Figure 1:
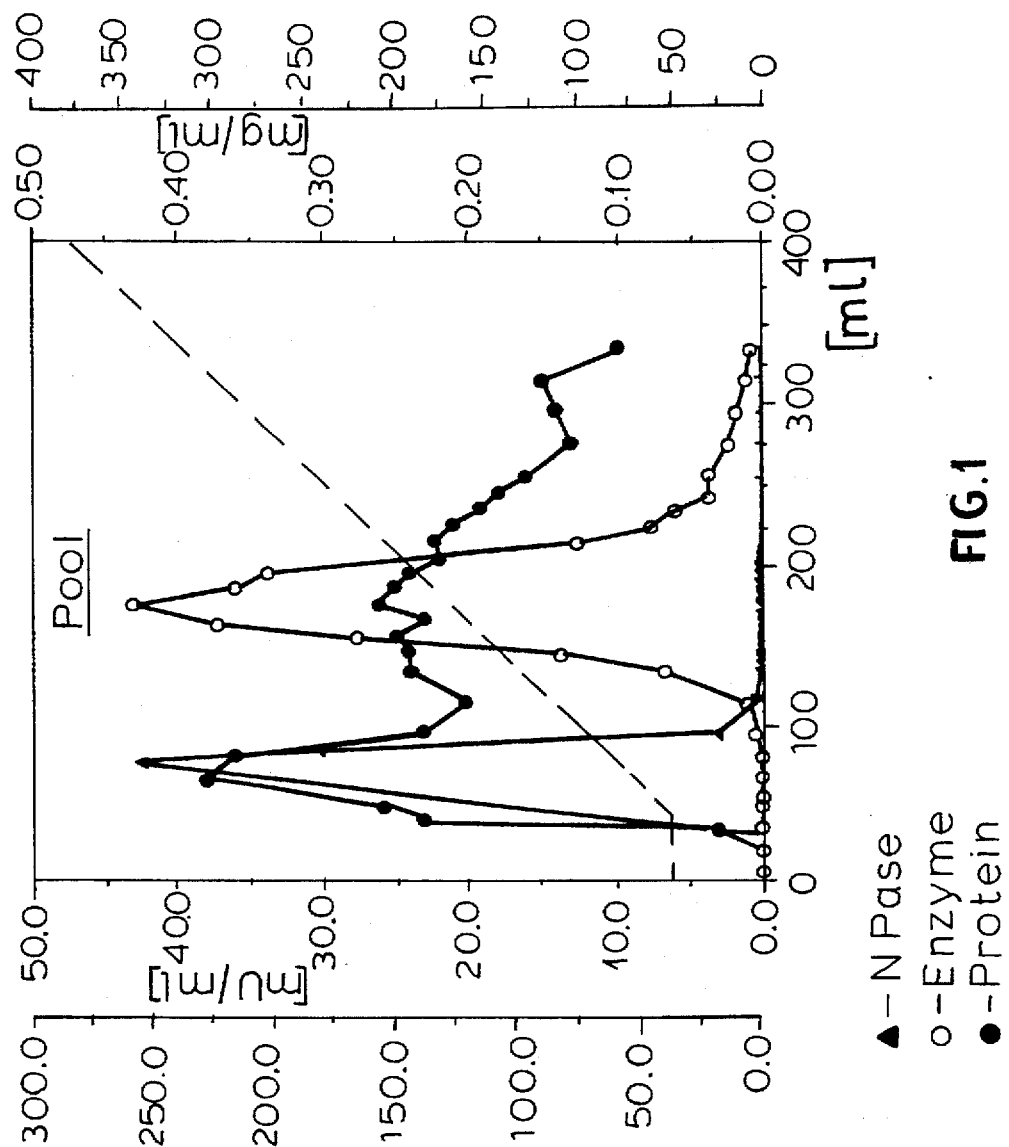
FIG. 1 is the chromatogram of the sepharose-Q-separation

Sucrose synthase from the rice is enriched 151 times with the yield of 5.4% (Table 1A). A greater loss is obtained by the precipitation with polyethyleneglycol 4000 (about 80% loss with 5 to 20% precipitation). Alternatively, an enzyme enrichment can be provided of the raw extract with the aid of an aqueous 2-phase system (PEG/Salt). Very effective are the batch adsorption on sephadex A50 and the subsequent anionic chromatography on sepharose-Q-fastflow with a purification factor of 43 in toto. Aside from this, the nucleotide diphosphatase and monophosphatase activity is completely separated out (FIG. 1) which is very important for the use of the sucrose-synthase in enzymatic synthesis.

The molecular weight of the native enzyme amounted to 362,000±7,000 Da, it is comprised of 4 subunits each of 90,000 Da and has no intermolecular or intramolecular disulfide bridges. The N-terminal aminoacid sequencing by an automated Edmand decomposition in a pulse liquid protein sequencer indicated that the N-terminal of the subunit is blocked. The isoelectric point of the native enzyme was at pH 6.16.

The purification of the saccharose-synthase was optimized based upon the starting amount of rice and the number of purification steps. Table 1B indicates that the yield with only slightly reduced purity could be increased to 21%. The purification encompassed instead of 6, only 4 steps, whereby the precipitation with 20% PEG 4000 and the batch adsorption on sephadex A50 were omitted. The purified enzyme is also free from nucleotide monophosphatases and nucleotide diphosphatases also after this purification.

TABLE 1A

PURIFICATION OF SUCROSE SYNTHASE FROM 800 G RICE

| Method | Volume [ml] | Protein [mg] | Activity [U] | Yield [%] | Purification Factor-Times |
|---|---|---|---|---|---|
| Disintegration | 704 | 5140 | 30.4 | 100 | 1 |
| PEG 4000 | | | | | |
| 5–20% (w/w) | 40 | 632 | 5.1 | 17 | 1.4 |
| Sephadex A50 | 250 | 135 | 8.9 | 29 | 11 |
| Sepharose Q | 80 | 17.6 | 4.5 | 15 | 43 |
| Superdex 200 | 18 | 1.8 | 1.6 | 5.4 | 154 |

TABLE 1B

PURIFICATION OF SUCROSE SYNTHASE FROM 6 KG RICE

| Method | Volume [ml] | Protein [mg] | Activity [U] | Yield [%] | Purification Factor-Times |
|---|---|---|---|---|---|
| Disintegration | 4555 | 15944 | 113.4 | 100 | 1 |
| PEG 4000 SUPERNATANT | | | | | |
| 5% (w/w) | 4500 | 10350 | 76.1 | 67 | 1.03 |
| Sepharose Q | 1300 | 1950 | 66.4 | 58.6 | 4.8 |
| Superdex 200 | 80 | 28.8 | 24.3 | 21.4 | 118.9 |

The investigation of the splitting reaction and synthesis reaction with sucrose synthase has indicated that 1. Sucrose-Synthase is suitable for the enzymatic synthesis of UDP-glucose, TDP-glucose, GDP-glucose and CDP-glucose from sucrose.
2. The combination of sucrose-synthase with other enzymes (see above) can be used for the enzymatic synthesis of secondary nucleotide sugars (UDP-galactose, UDP-glucouronic acid).
3. In the enzymatic synthesis of Oligosaccharides in the enzyme membrane reactor the use of sucrose-synthase for "cofactor regeneration" represents a significant simplification of the kinetic control.
4. The substrate spectrum of sucrose-synthase for Di-Tri- and Oligosaccharide as well as glucoside gives rise to hitherto not accessible activated Mono-, Di- and Oligosaccharides.
5. Other nucleotide sugars than UDP-glucose can be used in the synthesis reaction with fructose.
6. Fructose can be replaced with other sugars with β-furanose configuration as well as by sugar alcohols and other chemical compounds with structural similarity to β-furanose.

Below examples of the mode of action and use of the saccharose-synthase are described:

1. Substrate spectrum of the nucleosidediphosphate.

UDP, TDP, CDP, ADP and GDP were investigated. The reaction compositions contained:

550 μl Hepes-NaOH (200 mM, pH 7.2)
250 μl Sucrose (2 M)
100 μl Nucleosidediphosphate (15–90 mM)
100 μl purified Sucrose-synthase (21.1 mU/ml)

The reaction composition was incubated at 30° C. and stopped at different times (5 min. at 95° C.). After filtration of the sample through a 0.22 μm filter, the resulting nucleotide sugar was analyzed by means of ionpair HPLC.

The formation of UDP-glucose and TDP-glucose was quantified based upon calibration curves for the HPLC chromatogram (peak area/concentration).

Figure 2:
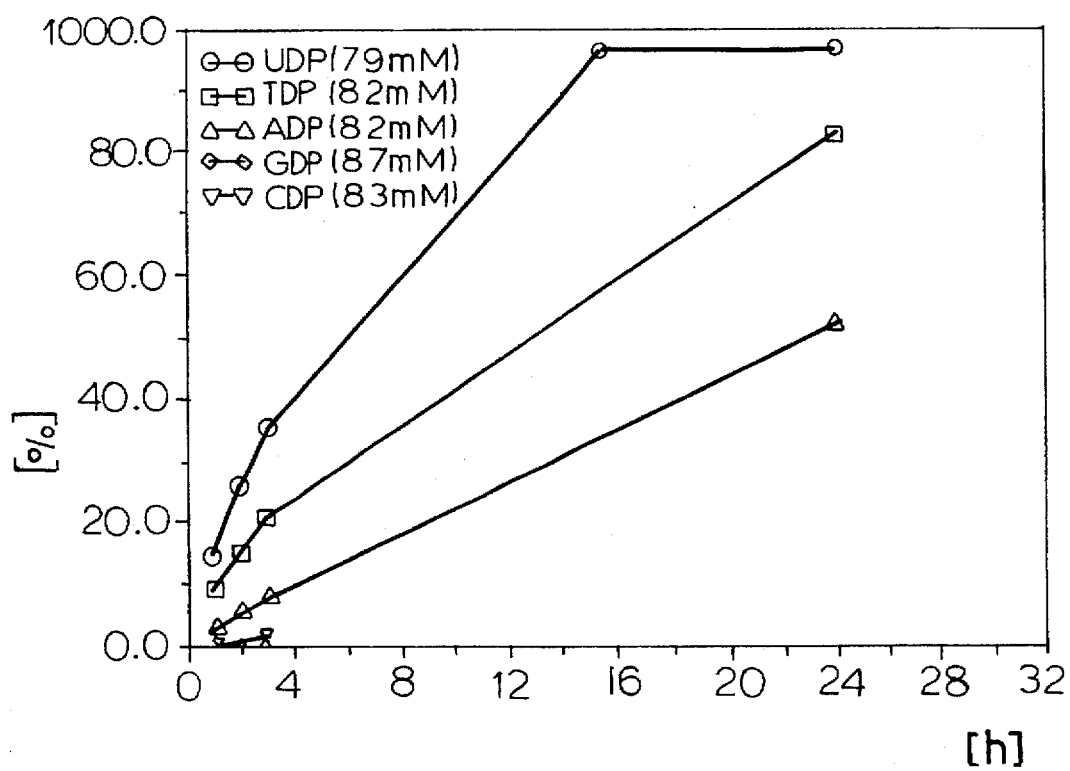
FIG. 2: shows the rate of NDP-glucose formation with different nucleotides.

FIG. 2 shows that the nucleosidediphosphate was accepted in the sequence UDP, TDP, ADP, CDP and GDP. The purified enzyme was free from nucleotidephosphatases (NPases, control without sucrose), which decompose the nucleosidediphosphates to the monophosphates or also to their bases. In the HPLC chromatogram, the peaks which arise for UMP, TMP, uridine and thymidine were recycled by suitable control test upon impurities on the substrate and by the decomposition of the nucleosidediphosphate by the heat treatment. After heat treatment of 1.57 mM UDP, 0.123 mM UMP results; of that 0.082 mM (5%) was already present as impurities in the UDP substrate.

From an investigation into the concentration characteristic with time of the syntheses of UDP-glucose and TDP-glucose, it is clear that with increasing quantities of enzymes the practically complete reaction of the nucleosidediphosphate to nucleotide sugar can be achieved in short reaction times.

Table 2 shows the reaction rates for the syntheses of UDP- and TDP-glucose together. With 0.16 mU enzyme, the space-time yield increases only slightly with-higher substrate concentrations. With 1.8 mU sucrose-synthase, after 3 hours, a 99% reaction calculated on the UDP concentration (1.57 mM) at starting can be achieved. This corresponded to a space-time yield of 0.21 g/l·h. With a higher UDP concentration (7.86 mM), the space time yield amounted to 0.4 g/l·h.

TABLE 2

Conversion of UDP and TDP to UDP- and TDP-Glucose with purified Sucrose Synthase from Rice and a Commercial Preparation from Wheat.

| Enzyme | Amount mU | UDP mM | UDP-Glucose mU | UMP mM | Conversion % | Time h | Peak Area % | Space-Time Yield g/l · h |
|---|---|---|---|---|---|---|---|---|
| Invention | 0.16 | 1.57 | 1.37 | 0.11 | 87.3 | 30 | 84.5 | 0.018 |
| " | 1.80 | 1.57 | 1.56 | 0.07 | 99.4 | 3 | 93.7 | 0.210 |
| " | 0.16 | 7.86 | 1.83 | 1.27 | 23.3 | 30 | 22.1 | 0.025 |
| Commercial | 0.20 | 1.57 | 1.31 | 0.21 | 83.4 | 24 | 83.5 | 0.022 |
| " | 0.20 | 7.86 | 2.38 | 0.79 | 30.3 | 24 | 30.0 | 0.040 |

| Enzyme | Amount mU | TDP mM | TDP-Glucose mM | TMP mM | Conversion % | Time h | Peak Area % | Space-Time Yield g/l · h |
|---|---|---|---|---|---|---|---|---|
| Invention | 0.16 | 1.64 | 0.80 | 0.23 | 48.8 | 30 | 50.3 | 0.011 |
| Commercial | 0.20 | 1.64 | 1.24 | 0.31 | 75.6 | 30 | 72.0 | 0.017 |

The space time yield for the synthese of TDP-glucose amounted to 0.011 g/l·h for 0.16 mU of enzyme at start; the conversion corresponded to 49% after 30 h for 0.16 mU enzyme. A further experiment indicated that the conversion of 8/2 mM TDP with 0.2 mU enzyme after 24 hours was increased to 80%.

For comparison, a commercial preparation of the saccharose-synthese from wheat was tested (specific activity 8.15 mU/mG). This enzyme showed similar space-time yields as the purified enzyme from rice. However, the HPLC chromatogram indicated the simultaneous formation of relatively large amounts of UMP and uridine through Nucleotidephosphatases (Table 2). These enzyme impurities are not present in purified enzyme from rice. The resulting UMP- and uridine peaks in the chromatogram can be recycled only by heating the specimens.

2. Buffer Spectrum

The buffer spectrum for the syntheses of UDP- and TDP-glucose was investigated with the purified sucrose-synthase from rice and the commercial enzyme from wheat. The following buffers were tested (all at 200 mM and pH 7.2, the pH buffer ranges are given):

| | |
|---|---|
| Mops-NaOH—NaCl | pH 6.25–8.15 |
| TES-NaOH—NaCl | pH 6.55–8.45 |
| Tris-HCl | pH 7.00–9.00 |
| Hepes-NaOH | pH 6.80–8.20 |
| $KH_2PO_4$—NaOH | pH 5.80–8.00 |
| $Na_2HPO_4$—$NaH_2PO_4$ | pH 5.80–8.00 |
| Imidazole | pH 6.20–7.80 |
| TEA-Hydrochloride-NaOH | pH 6.80–8.80 |

The Incubation composition contained:
550 µl Buffer (200 mM, pH 7.2)
250 µl Sucrose (2 M)
100 µl UDP (15.7 mM) or TDP (16.4 mM)
100 µl Enzyme solution Incubation and Analysis were carried out as described under 1.

It was found that the hitherto used hepes-NaOH-buffer was most suitable for the synthesis of UDP-glucose and TDP-glucose. For both enzymes, the Mops-buffer and the TES-buffer gave 60 to 80% residual activity. The commercial enzyme indicated, by contrast to the rice enzyme, in TEA-buffer, an about 30 to 40% higher residual activity. In the remaining buffers, both enzymes had a residual activity of less than 50%.

These results indicate that the selection of the buffers is significant to the activity of the sucrose-synthase and the determination of the pH optimum can be influenced thereby.

3. pH-Optimum

The following buffers were used for the determination of the pH optimum (all at 200 mM):

| | |
|---|---|
| Na-Citrate-Citric acid | pH 4.0–6.2 |
| $KH_2PO_4$—NaOH | pH 5.8–7.2 |
| Mops-NaOH—NaCl | pH 6.3–7.4 |
| Hepes-NaOH | pH 6.8–8.2 |
| TEA-hydrochloride-NaOH | pH 7.2–8.8 |

The incubation composition contained:
640 µl buffer (200 mM)
250 µl Sucrose (2 M)
100 µl UDP (15.7 mM) or TDP (16.4 mM)
10 µl Enzyme solution Incubation and analysis are affected as described under 1.

Both enzymes show different pH optima in dependence upon the buffer used.

With UDP as the substrate, both enzymes have a pH optimum between 5.5 and 5.7 with use of citrate buffer or phosphate buffer.

With use of the Hepes buffer and Mops buffer, the optimum for the UDP-glucose synthesis lies between pH 6.7 and 7.0.

For the synthesis of TDP-glucose this is in the same way; with citrate buffer or phosphate buffer the optimum lies between pH 5.8 and 6.2 and with Mops buffer or Hepes buffer between 6.5 and 6.8.

4. pH Stability

For determining the pH stability, the rice enzyme is incubated at different pH values in Hepes-NaOH-buffer (200 mM) and for different space-temperatures of different durations. The enzyme is then subjected to the usual activity test:

550 µl Hepes-NaOH (200 mM, different pH values)
250 µl Sucrose (2 M)
100 µl UDP (20 mM)
100 µl Enzyme solution After 1 h reaction time, the specimens were analyzed as described above with HPLC.

The purified sucrose-synthase from rice shows at pH 7.0 and 7.9 after 2 hours a residual- activity of >60%, which allows its use for the synthesis of UDP-glucose and TDP-glucose.

5. Temperature Optimum

For determining the temperature optimum, the rice enzyme was incubated at pH 6.5 (pH optimum) and different temperatures. Thereafter, the enzyme was subjected to the following activity test:

550 µl Buffer (200 mM, pH 6.5)
250 µl Saccharose (2 M)
100 µl UDP (20 mM)
100 µl Enzyme solution.

After 1 hour of reaction time, the samples were analyzed as described above with HPLC. Additionally, a respective control for each was incubated without enzymes and analyzed.

For the splitting of sucrose with UDP, the temperature optimum of the sucrose-synthase from rice at pH 6.5 was between 50° and 60° C.

6. Temperature stability

The enzyme retained after 5 hours at 37° C. its full activity, after 5 hours at 56° C. a residual activity of 37% was present.

8. Kinetics

Figure 10:
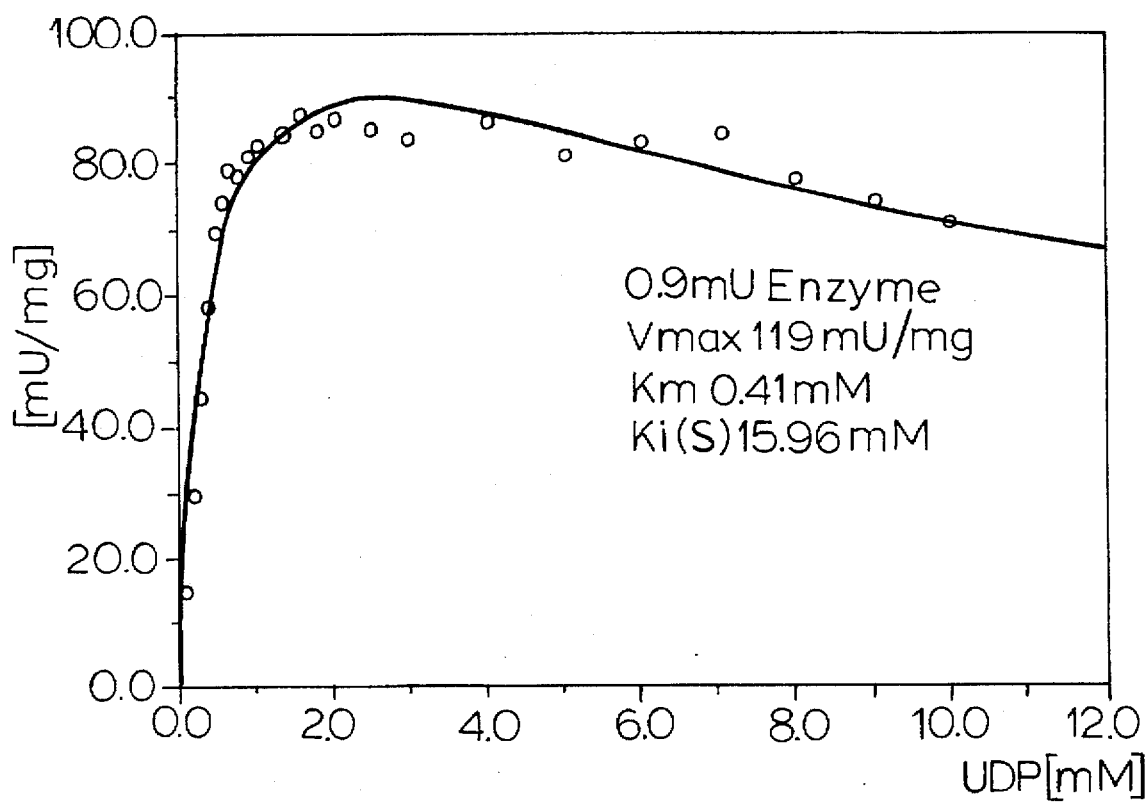
FIGS. 10–12 show curves of the kinetics of the synthesis reaction (I)
Figure 11:
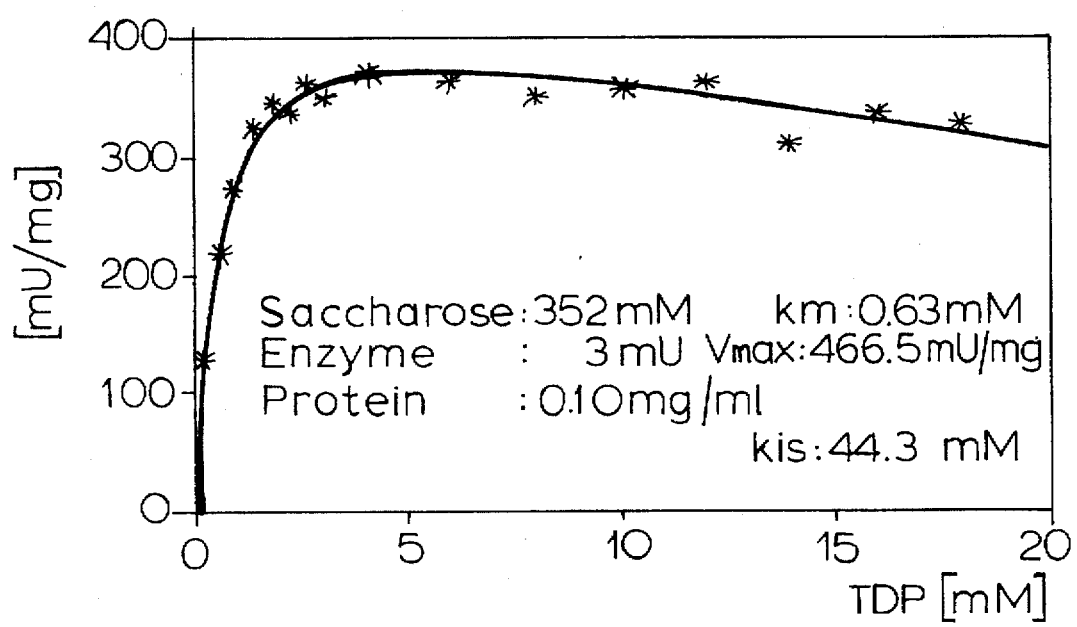
Figure 12:
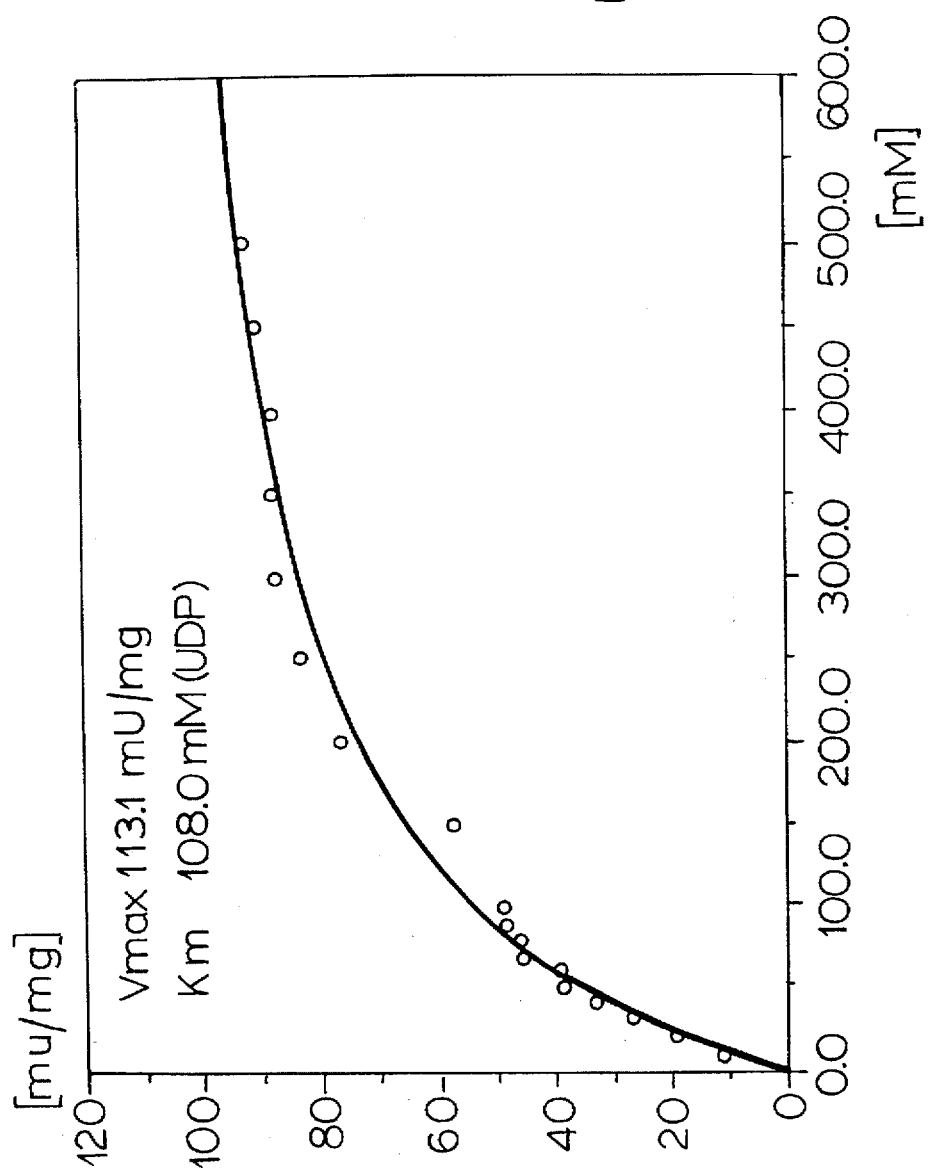

To determine $V_{max}$ and $K_m$ of the substrate, UDP or TDP was varied with constant sucrose concentration from 500 mM between 0 and 10 mM in the reaction mixture. With a constant UDP (2 mM) concentration, the sucrose was varied in the reaction composition between 0 and 500 mM. All reaction mixtures were incubated for 1 h at 30° C. and pH 6.5 (Hepes-NaOH 200 mM). The samples were treated as described above and analyzed with HPLC. The rice enzyme indicated for UDP a substrate excess inhibition (Ki(S)=16 mM with 0.9 mU enzyme) at a Km-value of 0.4 mM (FIG. 10). The Km-value for TDP amounted to 0.65 mM (FIG. 11). The substrate excess inhibition can be countered by higher enzyme quantities. The Km-value for saccharose amounted to 108 mM (FIG. 12).

9. Dependence on Divalent Metal Ions

Figure 13:
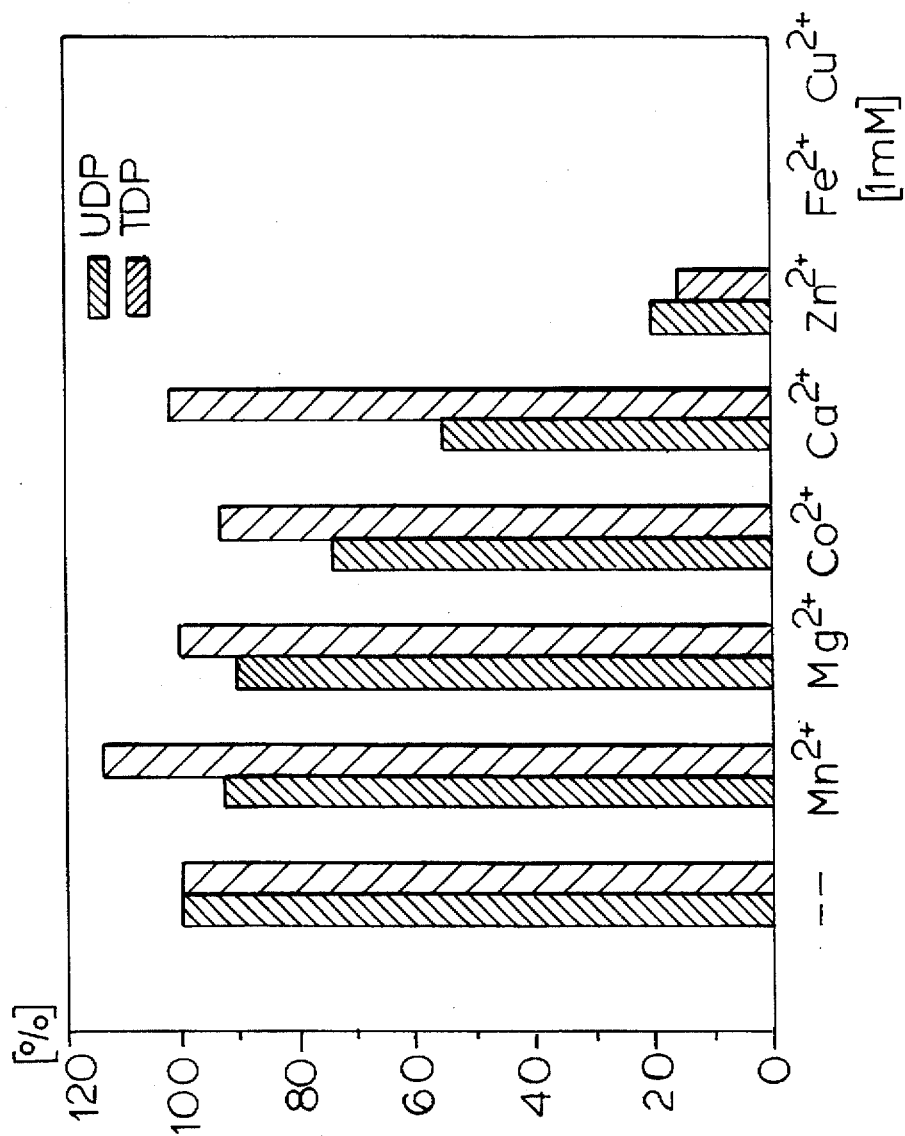
FIG. 13 shows the influence of metal ions on the enzyme activity.

FIG. 13 shows that in the presence of 1 mM of metal ions, for example $Mn^{2+}$ and $Mg^{2+}$ the activity of the saccharose synthase is influenced only slightly. A stimulation of the enzyme activity occurred with $Mn^{2+}$ and $Ca^{2+}$ with TDP as the substrate. In the presence of $Cu^{2+}$ and $Fe^{2+}$ the enzyme is completely inactivated.

10. Enzymatic Synthesis of UDP-glucose and TDP-glucose under Optimum Conditions The reaction composition contained:
550 µl Hepes-NaOH (200 mM, pH 7.2)
250 µl Saccharose (2 M)
100 µl Nucleosidediphosphate (UDP 100 mM or TDP 124 mM)
100 µl Purified sucrose-synthase (15 mU/ml)

The reaction composition was incubated with UDP at pH 7.0 or with TDP at pH 6.8 at 30° C. and stopped at various times (5 min at 95° C.). After filtering the specimens through a 0.22 Am filter, the resulting nucleotide sugar was analyzed by means of ionpair HPLC.

The formation of UDP-glucose and TDP-glucose was quantified with calibration curves for the HPLC chromatogram (peak area/concentration).

Figure 3:
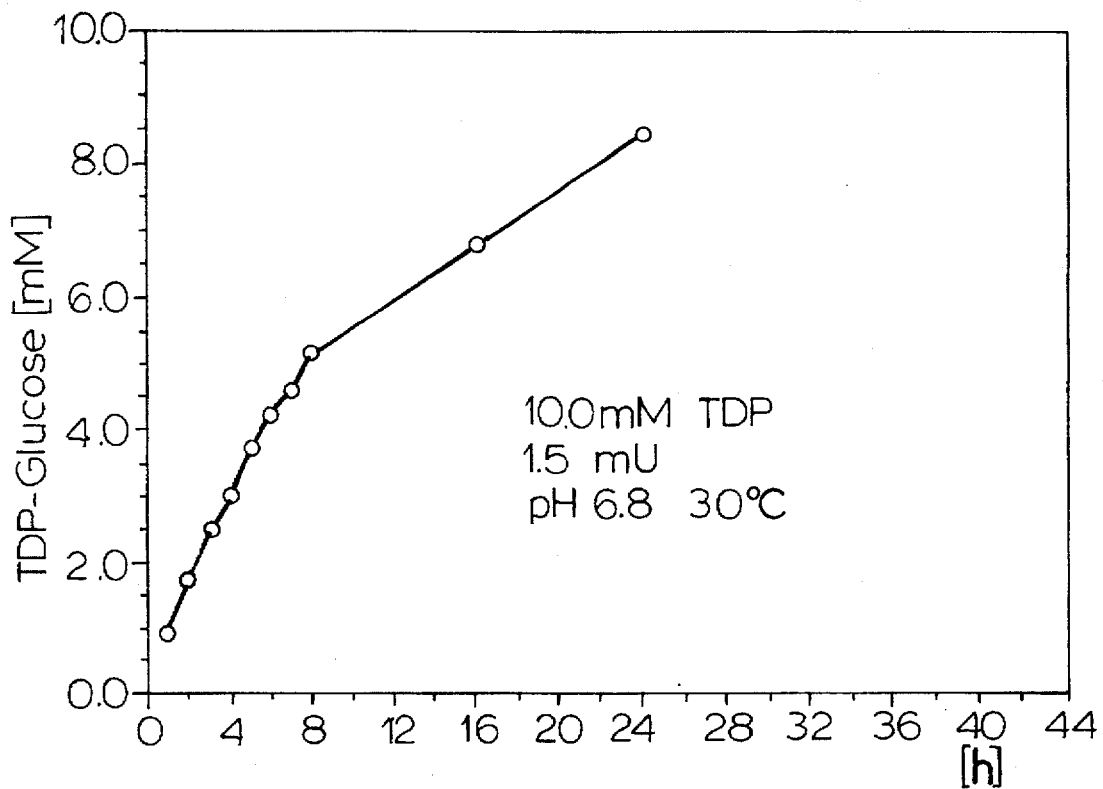
FIGS. 3 and 4 show the formation of TDP- and UDP-glucose with sucrose-synthase.
Figure 4:
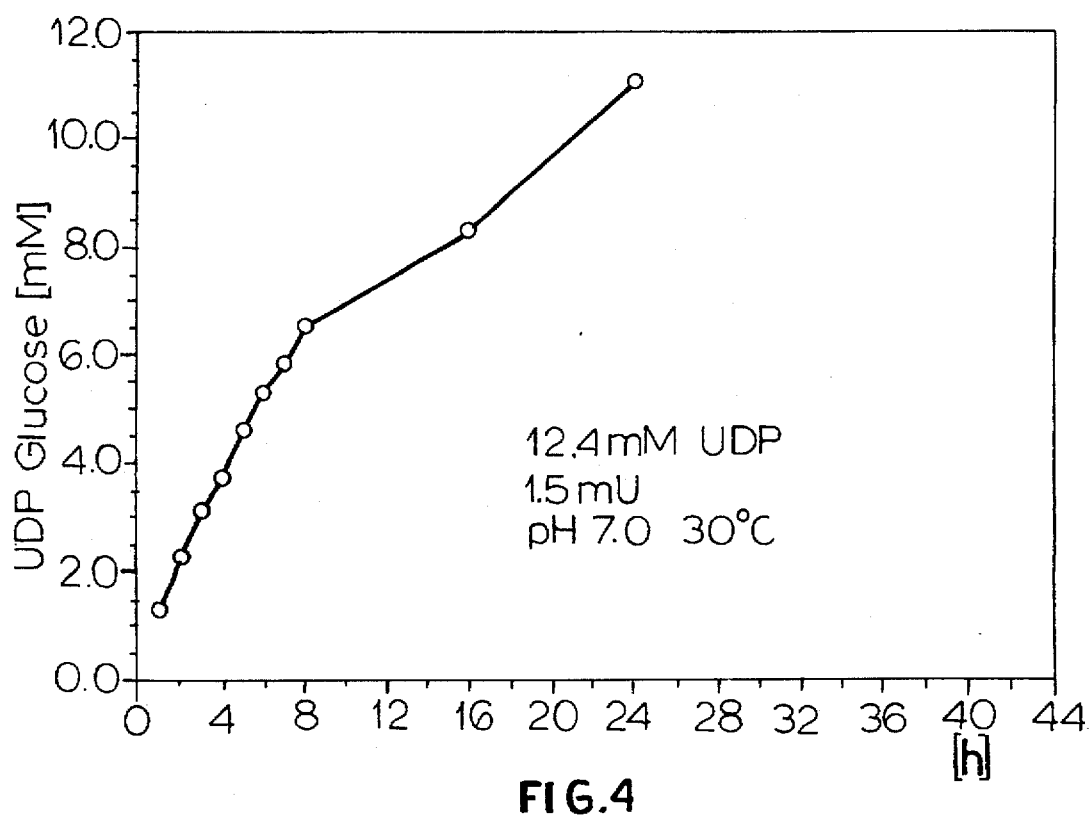

FIGS. 3 and 4 show that after 24 h 92% of the UDP is converted to UDP-glucose and 84% of the TDP to TDP-glucose.

Figure 14:
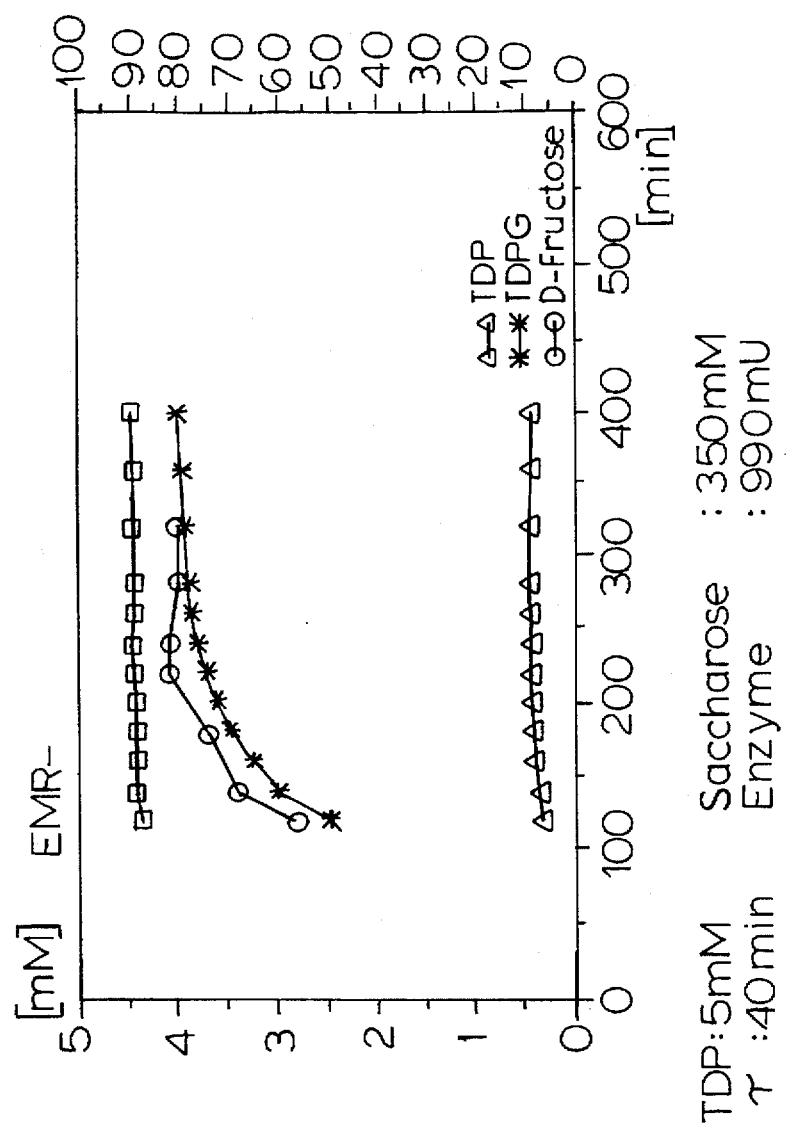
FIG. 14 show a diagram of the formation of TDP-glucose in the EMR-enzyme membrane reactor (EMR).

The purified sucrose-synthase was introduced into an enzyme membrane reactor (10 ml reactor-volume) for enzymatic synthesis of TDP-glucose. FIG. 14 shows the conversion of TDP to TDP-glucose and the concentrations of TDP, TDP-glucose and fructose at 5 mM TDP, 350 mM saccharose, 40 minutes residence time and 990 mU sucrose-synthase. The conversion amounted to 89.6% calculated on the TDP introduced. The theoretical space time yield for a one-liter reactor volume gave 98.1 g TDP-glucose per liter and day.

11. Substrate Spectrum of the Sucrose-Synthase for the splitting reaction (I)

For the splitting reaction of the sucrose-synthase, sucrose was replaced by other disaccharide or trisaccharide:

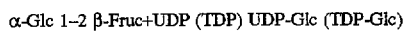

α-Glc 1-2 β-Fruc+UDP (TDP) UDP-Glc (TDP-Glc)

The concentration of the saccharide amounted to 75 to 500 mM in the reaction composition. 2 mM UDP or TDP and as a rule 10 to 80 mU enzyme were introduced. After 3 h at 30° C. and pH 7.2 (200 mM Hepes-NaOH), the reaction was stopped at 95° C. 5 min. The formation of nucleotide sugars was followed with HPLC and compared with a control (without enzyme).

Table 3 shows that the disaccharide isomaltulose (Palatinose) and the trisaccharide raffinose and melezitose can replace the saccharose.

12. Substrate Spectrum of the Sucrose-synthase from rice for the synthesis of Disaccharides.

A: Variation of the Nucleotide Sugar.

For the synthesis reaction the nucleotide sugars were varied:

UDP-Glucose+Fructose Saccharose+UDP

Initially only UDP activated sugar was introduced: UDP-galactose, UDP-N-acetylglucosamine, UDP-glucuronic acid, UDP-N-acetylgalactosamine.

The composition contained:

550 µl Buffer (200 mM, pH 7.5)

250 µl Fructose (40 M)

100 µl UDP-Sugar (20 mM)

100 µl Enzyme Solution

The composition was incubated for 2 hours at 30° C. and stopped for 5 minutes at 95° C. With HPLC, with comparison with a control (without enzyme) the development of UDP was followed.

Apart from UDP-glucose, UDP-N-acetylglucosamine and UDP-xylose can be reacted with the rice enzyme. (Table 4).

TABLE 3

TEST OF THE SUBSTRATE SPLITTING WITH PURIFIED SUCROSE-SYNTHASE FROM RICE AND UDP FOR SYNTHESIS OF ACTIVATED SUGARS

| Name | Linkage | Relative Activity % |
|---|---|---|
| Saccharose | α Glc 1-2 β Fruc | 100 |
| Saccharose-6'-P | | — |
| 2-deoxy-saccharose | | 55 |

TABLE 3-continued

TEST OF THE SUBSTRATE SPLITTING WITH PURIFIED SUCROSE-SYNTHASE FROM RICE AND UDP FOR SYNTHESIS OF ACTIVATED SUGARS

| Name | Linkage | Relative Activity % |
|---|---|---|
| Turanose | α Glc 1-3 β Fruc | — |
| Isomaltulose | α Glc 1-6 β Fruc | 1.0 |
| Lactulose | β Gal 1-4 Fruc | — |
| Trehalose | α Glc 1-1 α Glc | — |
| Maltose | α Glc 1-4 Glc | — |
| Isomaltose | α Glc 1-6 Glc | — |
| Laminaribose | β Glc 1-3 Glc | — |
| Cellobiose | β Glc 1-4 Glc | — |
| β-gentiobiose | β Glc 1-6 Glc | — |
| Mannobiose | α Man 1-3 Man | — |
| N'N'Diacetyl-chitobiose | β GlcNAc 1-4-GlcNAc | — |
| β-lactose | β Gal 1-4 β Glc | — |
| α-lactose | β Gal 1-4 α Glc | — |
| α-D-melibiose | α Gal 1-6 Glc | — |
| LacNAc | β Gal 1-4 GlcNAc | — |
| Ampicillin | | 2.4 |
| Chlorogenic acid | | — |
| Thiodigalactoside | | — |
| Thiodiglucoside | | — |
| p-aminophenyl1-β-L-fucopyranoside | | — |
| 3-0-β-D-galacto-pyranosyl-D-arabinose | | — |
| Octyl-β-D-glucopyranoside | | — |
| p-aminophenyl-β-D-galactopyranoside | | — |
| Raffinose | α Gal 1-6 α Glc 1-2 β Fruc | 3.8 |
| Melizitose | α Gal 1-3 β Fruc 2-1 α Glc | 0.4 |

TABLE 4

SUBSTRATE SPECTRUM OF THE PURIFIED SACCHAROSE SYNTHASE FROM RICE DIFFERENT UDP-SUGARS WERE USED WITH FRUCTOSE AS ACCEPTOR

| Name | Relative Activity % |
|---|---|
| UDP-glucose | 100 |
| UDP-galactose | — |
| UDP-N-acetylglucosamine | 1.8 |
| UDP-N-acetylgalaktosamine | — |
| UDP-glucuronic Acid | — |
| UDP-xylose | 1.7 |

12. Substrate Spectrum of the Saccharose-synthase from rice for the synthesis of Disaccharides.

B: Variation of the Acceptor.

For the synthesis reaction, the acceptor was varied. Apart from the natural acceptor, other diastereomers of D-fructose, like D-psicose, D-tagatose, D-sorbose were introduced. Further, several keytoses were systematically tested. Apart from Aldoses, nonsugar acceptors were also tested.

Table 5 indicates that the tested Diastereomers of D-fructose except from D-sorbose all are acceptors. L-sorbose, D-xylulose and the deoxyketoses are also acceptors of sucrose-synthase. Of the aldoses, D-mannose, D-lyxose and L-arabinose were acceptors. As acceptors, derivatives of glucose are available, e.g. 1,6 anhydro-β-D-glucose or octyl-β-D-glucopyranoside.

Disaccharide and trisaccharide (e.g. lactulose or raffinose) can also serve as acceptors. Of the nonsugar acceptors, derivatives of pyrrolidine can be introduced into the synthesis reaction of the sucrose synthase.

TABLE 5

SUBSTRATE SPECTRUM OF THE PURIFIED
SUCROSE-SYNTHASE FROM RICE
VARIOUS ACCEPTOR SUBSTRATES WERE
REACTED WITH UDP-GLUCOSE

| Name | Relative Activity % |
|---|---|
| D-fructose | 100 |
| Sedoheptulose Anhydride | 1.1 |
| Mannoheptulose | — |
| D-psicose | 14.1 |
| D-tagatose | 28.3 |
| D-sorbose | — |
| L-sorbose | 6.0 |
| D-ribulose | — |
| D-xylulose | 40.7 |
| L-xylulose | — |
| D-erythrulose | — |
| 5-keto-6-deoxy-D-fructose | 25.1 |
| 5,6-dideoxy-5-methyl-D-fructose | 19.0 |
| 5,6-dideoxy-D-fructose | 7.6 |
| 6-desoxy-L-sorbase | 8.8 |
| D-glucoheptose | — |
| β-D-allose | — |
| β-L-allose | — |
| D-altrose | — |
| D-glucose | — |
| L-glucose | — |
| D-mannose | 3.9 |
| L-mannose | — |
| L-gulose | — |
| D-idose | — |
| L-idose | — |
| D-galactose | — |
| L-galactose | — |
| α-D-talose | — |
| D-ribose | — |
| L-ribose | — |
| D-arabinose | — |
| L-arabinose | 3.2 |
| D-xylose | — |
| L-xylose | — |
| D-lyxose | 14.7 |
| D-sorbitol | — |
| D-arabitol | — |
| L-arabitol | — |
| L-ascorbic acid | — |
| 1,6-Anhydroglucose | 9.1 |
| n-octyl-β-D-glucopyranoside | 0.5 |
| Hydroxypyruvate | — |
| 3-Hydroxybenzaldehyde | — |
| 3-Hydroxy-tetrahydrofuran | — |
| Tetrahydro-3-furan-methanol | — |
| S(+)-2-(hydroxymethyl)-pyrrolidine | — |
| 3-hydroxypyrrolidine | 6.3 |
| 3-hydroxy-N-methyl-pyrrolidine | 1.9 |
| 1-ethyl-3-hydroxy-pyrrolidine | 10.4 |
| 3-pyrrolidino-1,2-propandiol | 9.6 |
| N-(2-hydroxymethyl)piperidin | 9.4 |
| Tropin | 10.3 |
| Turanose | 0.5 |
| Lactulose | 12.3 |
| Raffinose | 8.4 |
| Isomaltulose | 3.1 |
| β-lactose | — |
| Melizitose | 0.6 |

13. Enzymatic Synthesis of UDP-Galactose and N-Acetyllactosamine according to the Diagram of FIG. 6

Figure 5:
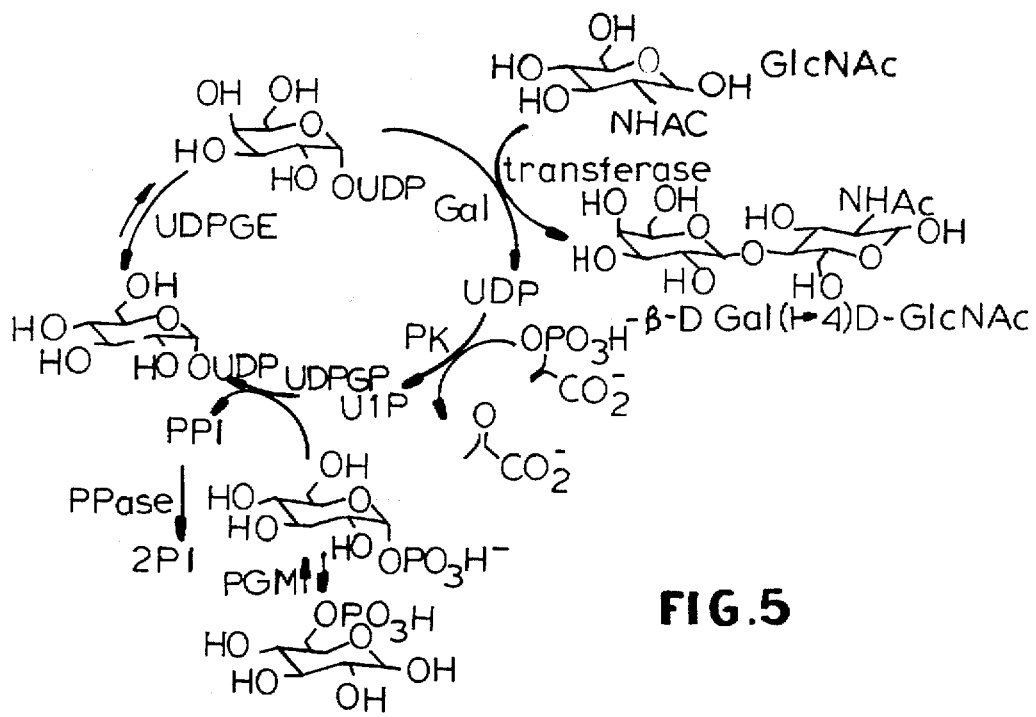
FIGS. 5 and 6 show reaction schemes for the enzymatic synthesis of N-acetyllactosamine (according to Wong)
Figure 6:
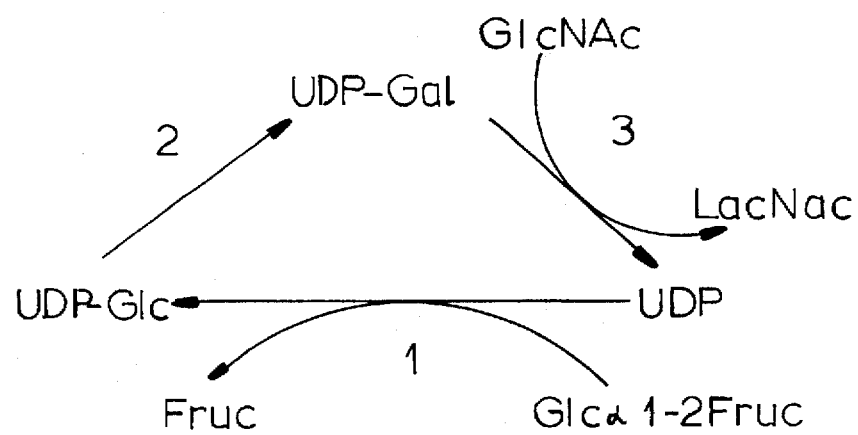

UDP-galactose and N-acetyllactosamine were produced according to FIG. 6 (FIG. 5 shows the synthesis cycle according to WONG)

Composition:
677 μl Hepes-buffer (50 mM, pH 7)
100 μl UDP (100 mM)
100 μl Saccharose
123 μl Enzyme (10 mU in composition)

Figure 7:
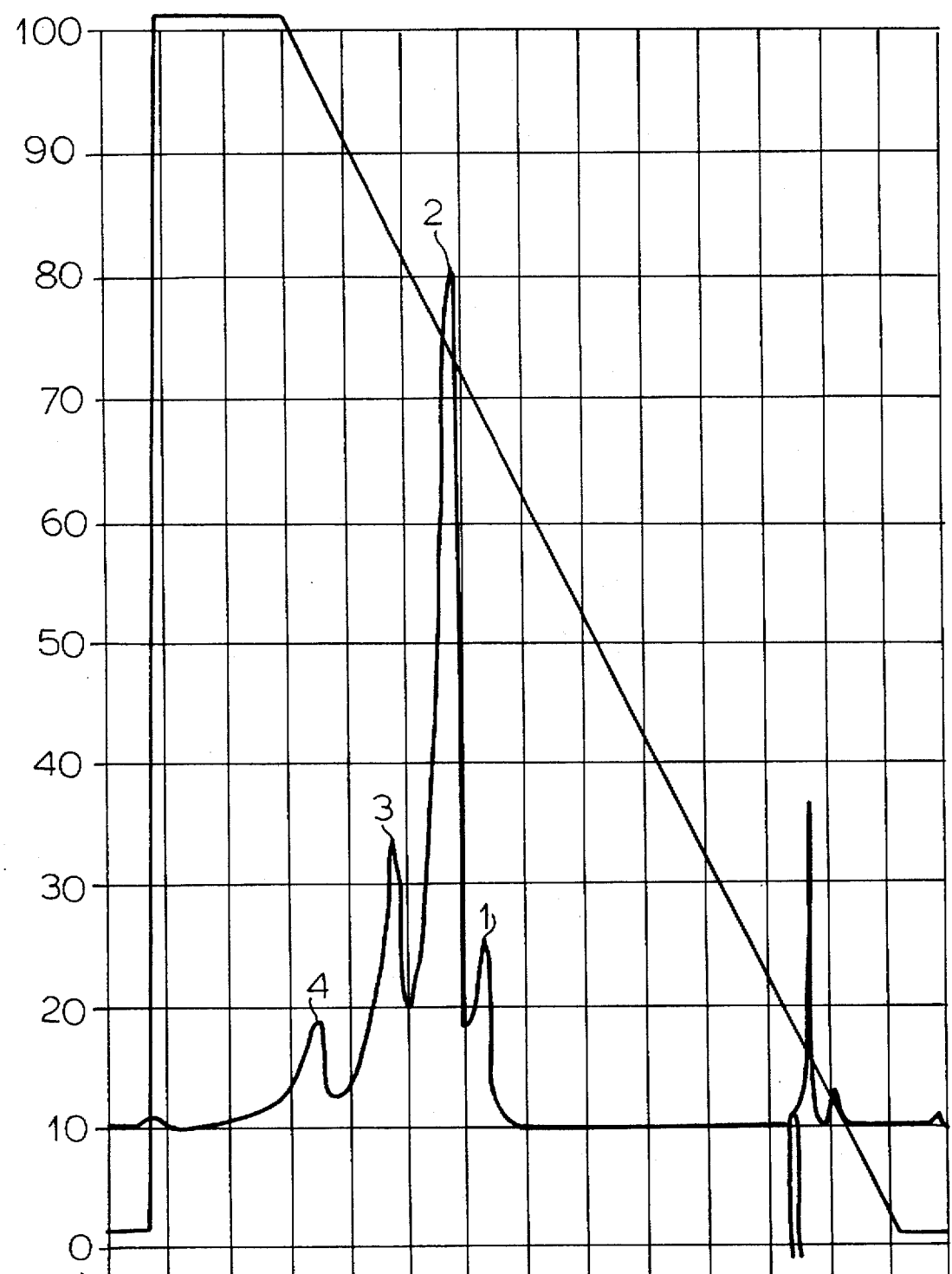
FIGS. 7 and 8 show a nucleotide-chromatograms of the product mixture (Step 1 and 2 according to FIG. 6) after the inactivation of the enzyme.

After 3 hours of incubation at 30° C., 80% of the UDP was converted to UDP-glucose as determined by HPLC analysis. Thereafter, 100 mU UDP-galactose-epimerase was added and incubated at 30° C. overnight. FIG. 7 shows that UDP-galactose results from UDP-glucose. Since the equilibrium of the UDP-galactose-epimerase lies strongly on the side of UDP-glucose, UDP-glucose/UDP-galactose ratios of 0.3 are expected (see the peak height ratios of UDP-glucose/UDP-galactose in FIG. 7).

UDP-galactose can also be enzymatically produced by simultaneously incubating the requisite enzyme in the composition.

Composition:
500 mM Sucrose
1–10 mM UDP
3–30 mU Sucrose-synthase
200 mU UDP-gal-epimerase
All in 200 mM Hepes-buffer pH 7.2

Figure 8A:
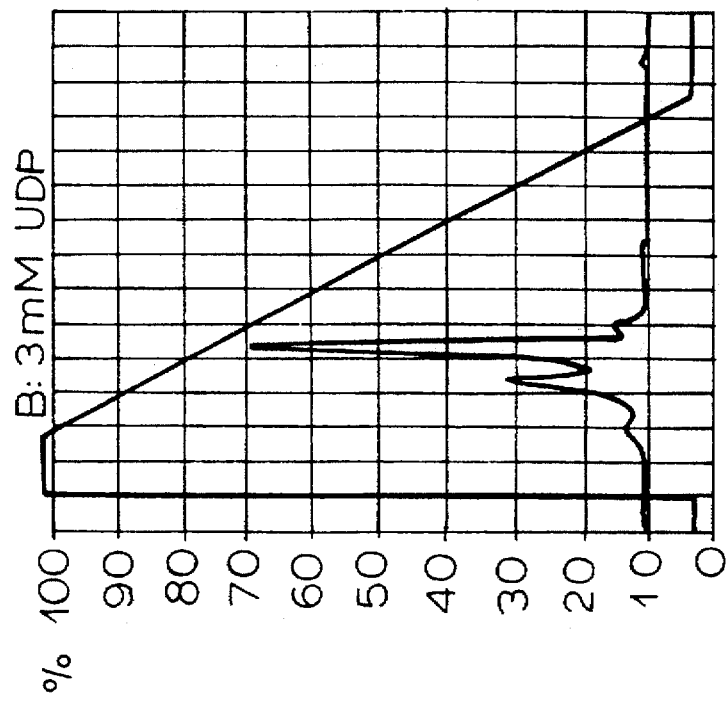
Figure 8B:
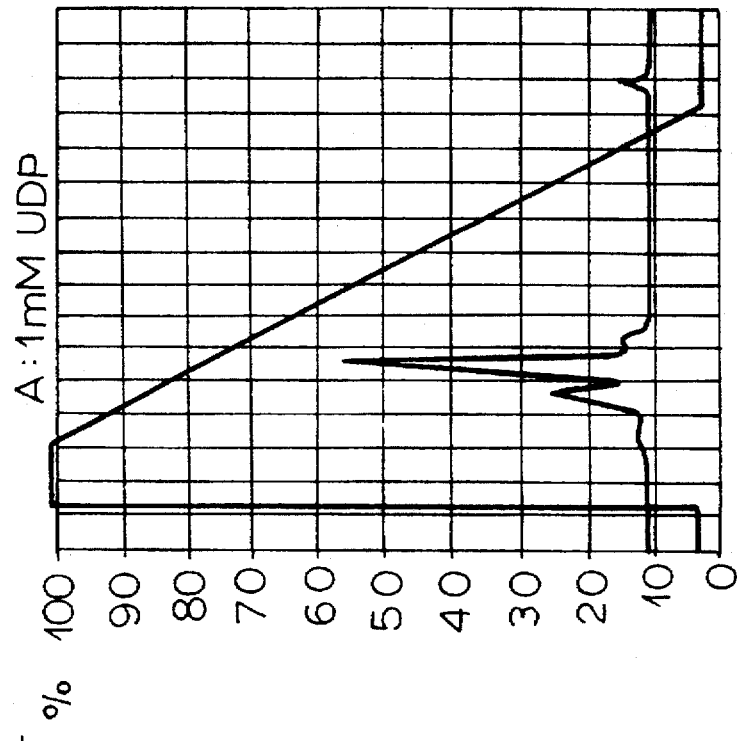

The results are documented in FIG. 8.

For enzymatic synthesis of N-acetyllactosamine, the following test was carried out.

1 mM UDP
1 mM MnCl$_2$
5 mM N-acetylglucosamine
500 mM saccharose
200 mU UDP-gal-epimerase
100 mU β-1,4-galactosyltransfer
120 mU sucrose-synthase
All in 200 mM Hepes-NaOH-buffer pH 7.2 at 30° C. overnight.

Figure 9:
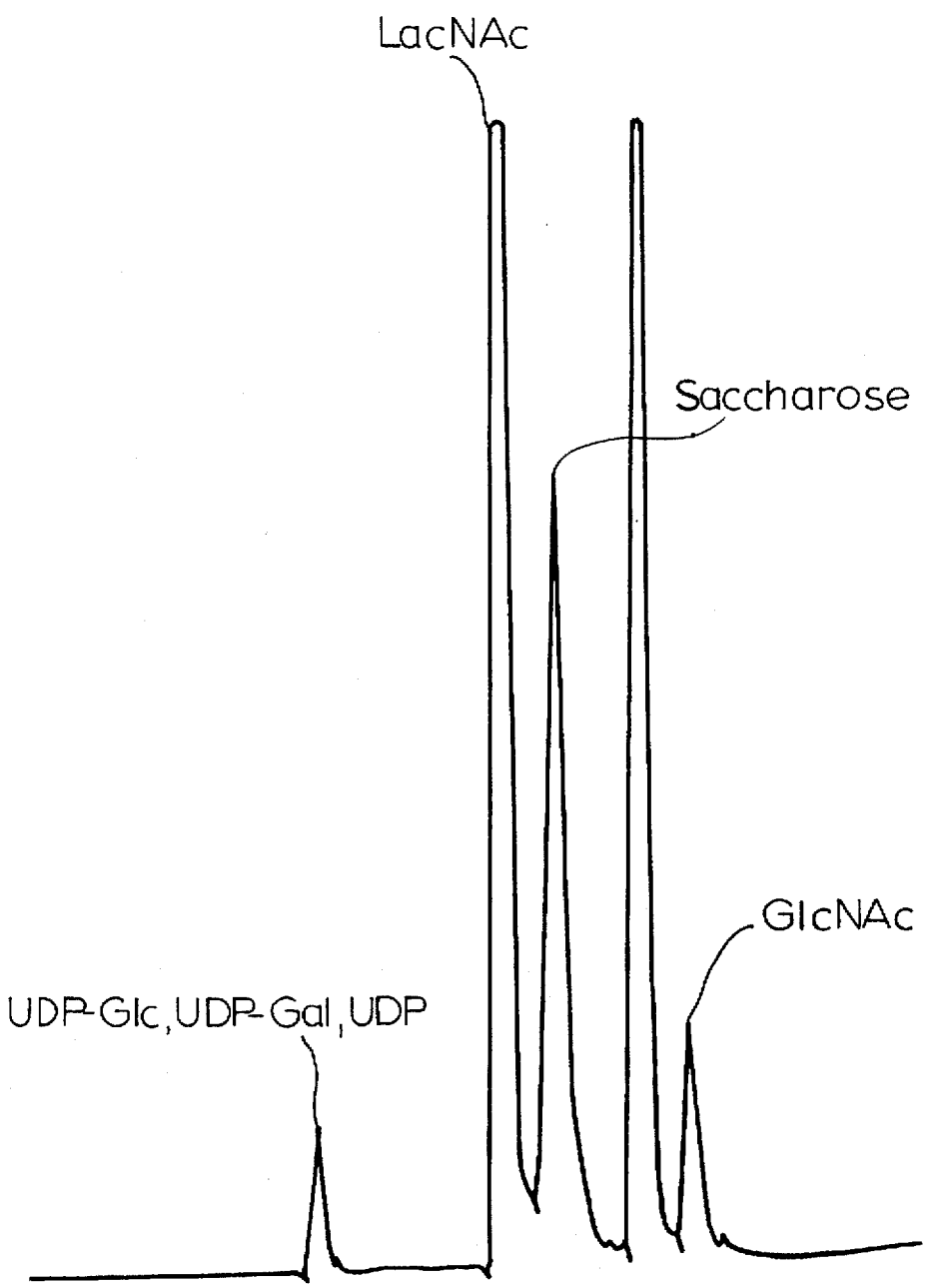
FIG. 9 show the HPLC-chromatogram of the product mixture (complete cycle according to FIG. 6)

FIG. 9 shows that N-acetyllactosamine is formed with the aid of the three enzymes (FIG. 6). The conversion amounted to 80% based upon the starting concentration of N-acetylglucosamine.

In the previous tests, sucrose-synthase isolated from rice grains were used; however sucrose-synthase obtained from wheat, inter alia, observing the requirements of the invention and usable for single stage formation of activated monosaccharide can be employed as well.

What is claimed is:

1. A process for producing sucrose synthase with a nucleotide phosphatase content which is less than or equal to 0.1%, which comprises the steps of:

(a) swelling rice, corn or wheat grains in a solution;

(b) mechanically disintegrating the swollen rice, corn or wheat grains in said solution;

(c) treating the disintegrated swollen rice, corn or wheat grains to separate a liquid containing enzyme from solids;

(d) charging a liquid containing the enzyme on a Sepharose-Q-column at a pH of 8, subjecting said phase to linear gradient elution with 50 to 500 mM of KCl and collecting a fraction containing the enzyme; and (e) chromatographing the collected enzyme fraction in a gel filtration column to obtain the sucrose synthase.

2. The process for producing sucrose synthase defined in claim 1 wherein according to step (a) rice grains are swollen in solution.

3. The process for producing sucrose synthase defined in claim 1 further comprising the steps of:

following step (c), fractionally precipitating protein found in said liquid obtained in step (c) to form a pellet while the enzyme remains dissolved in the liquid, adsorbing the liquid containing the enzyme on a sephadex A 50 adsorbent and eluting stepwise the enzyme from the adsorbent with a Hepes-NaOH eluent at a pH of 7.2 and then with a Hepes-NaOH eluent containing KCl at a pH of 7.2 to obtain a phase with enzymatic activity which is then purified according to steps (d) and (e).

4. A process for the preparation of N-acetyl-lactosamine, which comprises the steps of:

(a) splitting sucrose with UDP in the presence of a purified sucrose synthase which can be used for the synthesis of nucleotide sugars on an industrial scale in whose HPLC chromatogram, nucleotide phosphatases are not detectable at a level greater than 0.1% and which shows no activity decrease after five hours at 37° C. to obtain UDP-glucose and fructose;

(b) epimerizing the UDP-glucose in the presence of UDP-galactose epimerase to obtain UDP-galactose; and (c) coupling the UDP-galactose with N-acetylglucosamine in the presence of beta-1,4-galactosyltransferase to obtain the N-acetyl-lactosamine.

5. The process defined in claim 4 wherein according to step (a) splitting the sucrose with UDP takes place at about 30° C.

6. The process defined in claim 4 wherein according to step (b) epimerizing the UDP-glucose takes place at about 30° C.

7. The process defined in claim 4 wherein steps (a), (b) and (c) are carried out in a buffer solution at a pH of about 7 to 7.2.

* * * * *